United States Patent
Sadkhin

(10) Patent No.: US 6,425,860 B1
(45) Date of Patent: Jul. 30, 2002

(54) THERAPEUTIC AND DIAGNOSTIC METHOD AND APPARATUS

(76) Inventor: Grigory Sadkhin, 1776 W. 13th St., Brooklyn, NY (US) 11223

( * ) Notice: Subject to any disclaimer, the term of this patent is extended or adjusted under 35 U.S.C. 154(b) by 1250 days.

(21) Appl. No.: 08/513,610

(22) Filed: Aug. 16, 1995

(51) Int. Cl.$^7$ ................................................. A61B 3/00
(52) U.S. Cl. .............................. 600/300; 606/4; 607/89
(58) Field of Search ................................. 351/200, 205, 351/206, 212, 221, 246; 606/2–19; 607/88–92; 128/630; 600/300

(56) References Cited

U.S. PATENT DOCUMENTS

| | | | | |
|---|---|---|---|---|
| 4,394,074 A | * | 7/1983 | McMahon | 351/206 |
| 4,907,586 A | * | 3/1990 | Bille et al. | 606/5 |
| 5,098,426 A | * | 3/1992 | Sklar et al. | 606/5 |

FOREIGN PATENT DOCUMENTS

| | | |
|---|---|---|
| DE | 7620542 | 12/1976 |
| DE | 8711668 | 2/1988 |
| DE | 3724283 | 5/1989 |
| DE | 3902410 | 8/1990 |
| DE | 4221038 | 1/1993 |
| DE | 4321796 | 1/1994 |
| FR | 2461481 | 2/1981 |

OTHER PUBLICATIONS

"Tridodignosis" by E.S. Velkhover and N.B. Shulpina, *Meditsina*, Moscow, 1988, p 228.
"Iridodiagnosis and Its Improtance For Phytotherapy" by V.V. Krivenko and G.P. Potebnya, edited by A.M. Grodzinskiy, Academy of Sciences of U.S.S.R., Kiev, *Nauk. Dumka*, 1988, p. 93.
B. Jensen, "Iridology Simplified" Iridologists International, 1980.

* cited by examiner

*Primary Examiner*—David M. Shay
(74) *Attorney, Agent, or Firm*—R. Neil Sudol; Coleman Sodol Sapone, P.C.

(57) ABSTRACT

A method for treating a patient comprises selecting a zone of a patient's iris to be treated, monitoring the patient's eye to determine a position of the selected zone, and, in accordance with the determined position of the zone, directing energy of a predetermined type and a predetermined magnitude toward the zone. The iris zone is selected in part by automatically scanning the patient's iris to generate a signal encoding patterns in the iris, and automatically comparing pattern data in the signal with previously stored pattern data to derive diagnostic information pertaining to the individual patient. The diagnosis and treatment selection are made by a computer programmed with statistical data correlating iris patterns of hue and light or darkness levels with physiological states of different organs and with possible treatments to counter undersirable conditions.

5 Claims, 4 Drawing Sheets

THERAPEUTIC AND DIAGNOSTIC METHOD AND APPARATUS

BACKGROUND OF THE INVENTION

This invention relates to a therapeutic method. This invention also relates to an associated diagnostic method. This invention also relates to an apparatus for effecting diagnosis and/or treatment of a patient.

In a well established practice, diagnoses are made by examining the pattern of light, darkness and hue of a person's iris. This art or science is known as iridology. Practitioners apparently consult iris charts to determine which organs may be adversely affected by disease or which may even be in a weakened condition, for example, from inflammation or stress. Various types of treatment may be attempted, including, for example, instituting variations in the patient's diet. Further information regarding the background, practice, theory and uses of iridology may be gleaned from the booklet "Iridology Simplified," by Bernard Jensen (1980), published by Iridologists International of 24360 Old Wagon Road, Escondido, Calif. 92027.

OBJECTS OF THE INVENTION

An object of the present invention is to provide a new method for the therapeutic treatment of individuals.

Another object of the present invention is to provide an apparatus for carrying out the method.

Another, more particular, object of the present invention is to provide a method and/or an apparatus for therapeutic treatment via the iris.

A further object of the present invention is to provide a method for diagnosing an individual via patterns in the individual's iris.

Another object of the present invention is to provide apparatus for diagnosing an individual via patterns in the individual's iris.

These and other objects of the present invention will be apparent from the drawings and detailed descriptions herein.

SUMMARY OF THE INVENTION

A method for treating a patient comprises, in accordance with the present invention, selecting a zone of a patient's iris to be treated, monitoring the patient's eye to determine a position of the selected zone, and, in accordance with the determined position of the zone, directing energy of a predetermined type and a predetermined magnitude toward the zone.

The iris zone may be selected in part by automatically scanning the patient's iris to generate a signal encoding patterns in the iris, and automatically comparing pattern data in the signal with previously stored pattern data to derive diagnostic information pertaining to the individual patient. The iris treatment zone may then be selected automatically in response to the diagnostic information. Preferably, the diagnosis and treatment selection is made by a computer programmed with statistical data correlating iris patterns of hue and light or darkness levels with physiological states of different organs and with possible treatments to counter undersirable conditions.

In accordance with the present invention, it is possible to automatically select characteristics of the energy applied, including intensity and duration of application, to treat a patient. Where the energy is waveform energy such as light or, more generally, electromagnetic energy, or acoustic energy, characteristics such as frequency and wavelength, as well as possibly polarization, may be varied according to the diagnostic information.

The scanning of the patient's iris may be implemented, in accordance with the present invention, by attaching a scanner apparatus to the patient's head and operating the scanner apparatus to generate the signal. For example, the scanner may be a video camera producing a video signal.

Where the stored pattern data is stored in a memory of a digital computer, the invention contemplates digitizing the pattern-encoding signal and transmitting the digitized signal to the computer.

According to another feature of the present invention, the patient's eye is automatically scanned to determine the position of the selected zone. For example, at least one video camera may be operated to generate a video signal encoding external structures of the patient's eyeball, including the patterns of the iris. The information in the video signal is automatically compared with previously stored video data as to the patient's eye to produce positional data. Thus, the location of the target zone of the iris is determined in real time to ensure that the energy directed towards this iris impinges on the selected target zone.

A method for diagnosing a patient comprises, in accordance with the present invention, automatically scanning a patient's iris to generate a signal encoding patterns in the iris, and automatically comparing pattern data in the signal with previously stored pattern data to derive diagnostic information pertaining to the individual patient.

As discussed above, the diagnostic information may be used to determine a treatment of the patient by applying a controlled amount of electromagnetic (light), thermal, and/ or acoustic energy to at least one zone of the patient's iris.

The diagnostic information derived by the scanning of the patient's iris may be printed out for inspection, storage or any other purpose.

An apparatus for treating a patient comprises, in accordance with the present invention, monitoring componentry for monitoring a patient's eye to determine a position of a preselected zone of the patient's iris, and an energy applicator operatively connected to the monitoring componentry for directing energy of a predetermined type and a predetermined magnitude toward the zone.

According to another feature of the present invention, the apparatus may further comprise a scanner for automatically scanning the patient's iris to generate a signal encoding patterns in the iris. Diagnostic componentry may be operatively connected to the scanner for automatically comparing pattern data in the signal with previously stored pattern data to derive diagnostic information pertaining to the individual patient. The diagnostic componentry is operatively connected to the energy applicator for at least partially controlling operation thereof.

According to a further feature of the present invention, the diagnostic componentry may include or be connected to means for automatically selecting the target treatment zone of the iris in response to the diagnostic information. The diagnostic or treatment selection componentry may further include means for automatically selecting characteristics of the energy, including intensity and duration of application, in response to the diagnostic information.

The scanner may be provided with straps or bands or other gear for attachment to the patient's head.

The present invention provides a new method and associated apparatus for the therapeutic treatment of individuals.

Controlled and limited amounts of energy are applied to selected zones of the iris to counteract undersirable conditions in corresponding organs of a patient.

The present invention also provides a method for the automated diagnosis of an individual via patterns in the individual's iris.

DETAILED DESCRIPTION

Figure 1:
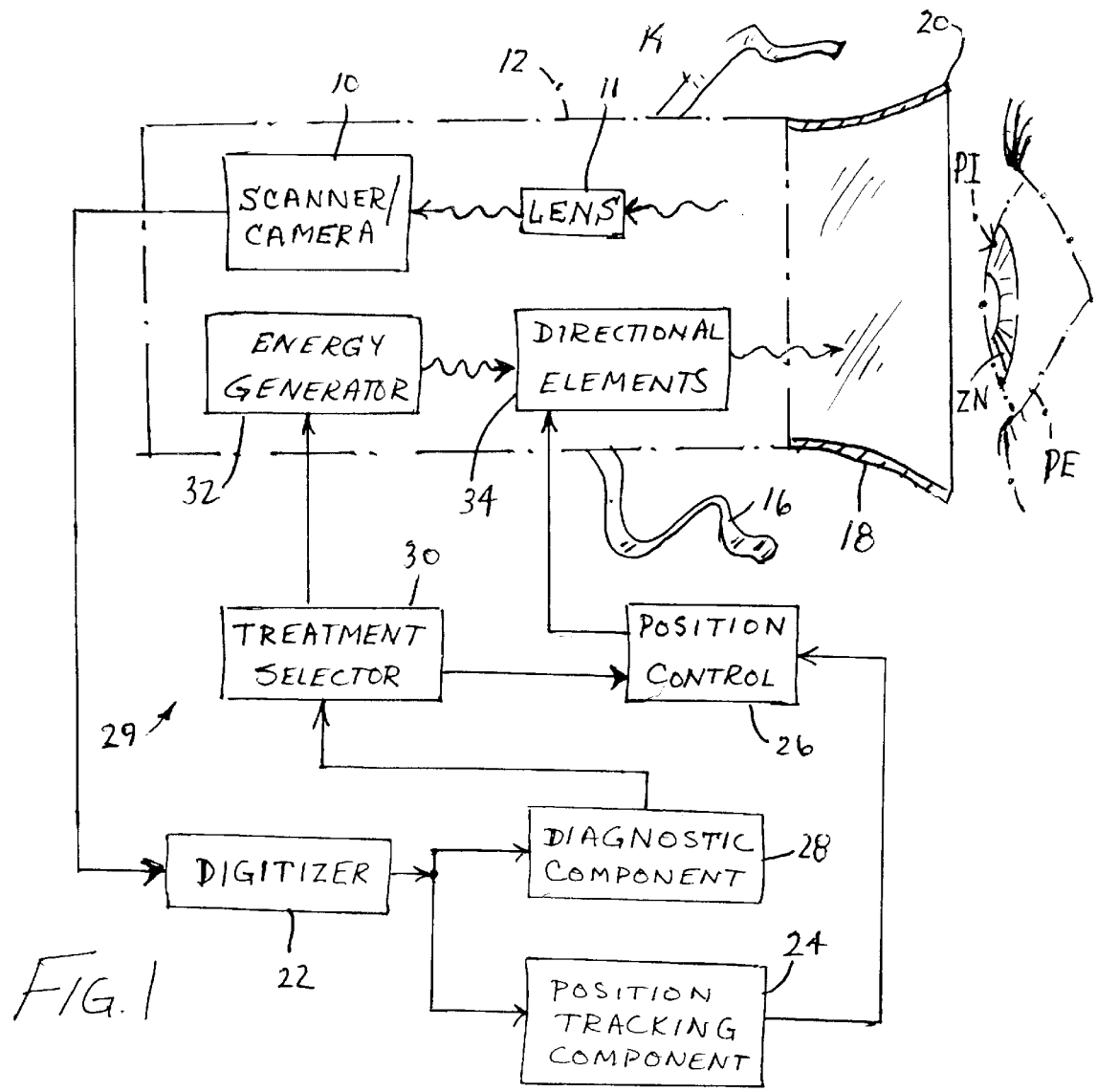
FIG. 1 is basically a block diagram of a diagnostic and therapeutic apparatus in accordance with the present invention.

As illustrated in FIG. 1, an apparatus for diagnosing and treating a patient comprises a scanner 10 in the form of a video camera or charge coupled device (CCD) for automatically and continuously monitoring a patient's eye PE. Video camera 10 receives light energy focused by a lens 11 and is disposed therewith inside a housing 12 which is provided with attachment elements such as bands 14 and 16 for fastening the housing to a patient's head. (not shown). A forward end of housing 12 is provided with a skirt 18 which is engageable about a rim 20 with skin surfaces (not shown) about the patient's eye PE.

Video camera 10 is operatively connected to a digitizer 22 in turn connected to a position tracking unit 24. In response to a digitized video signal at an output of digitizer 22, position tracking unit 24 monitors the angular position of the patient's eye and feeds data defining that position to a position control unit 26. The digitized video signal generated by video camera 10 and digitizer 22 encodes patterns in the patient's iris PI. Those patterns are defined by variations in lightness and color of fibrous elements of the iris.

Digitizer 22 is also connected at an output to a diagnostic component 28 which automatically compares pattern data in the digitized video signal with previously stored iris pattern data to derive diagnostic information pertaining to the individual patient. The stored data is a statistical compilation of different patterns of light and color in previously examined irises. The patterns of iris fibers in the previously examined irises are correlated with diagnostic information according to accepted principles of iridology. For example, relatively light rings or dark streaks in an iris may be correlated with weaknesses or abnormal conditions of respective organs.

Diagnostic component 28 is operatively connected to energy applicator componentry 29 including a treatment selector 30 and an energy generator 32. Diagnostic component 28 controls energy applicator componentry 29 to direct energy of a predetermined type and a predetermined magnitude toward a selected zone ZN of the patient's iris.

In response to diagnostic information from component 28, treatment selector 30 automatically chooses zone ZN, as well as the amount of energy. Target treatment zone ZN is selected in accordance with the principles of iridology. For example, if patterns in the iris indicate a particular weakness or abnormal condition of an internal organ, a zone ZN of the eye corresponding to that organ is selected to receive an amount of energy produced by energy source or generator 32 in response to instructions from treatment selector 30. Treatment selector 30 activates energy generator 32 to deliver energy of an intensity and duration (or multiple intensities and durations) via directional or guide elements 34 to the selected zone ZN of the patient's iris PI.

Energy generator 32 and directional elements 34 may be both disposed in housing 12. Directional elements 34 are controlled by unit 26 to direct therapeutic energy from generator 32 to the selected iris zone ZN.

Figure 2:
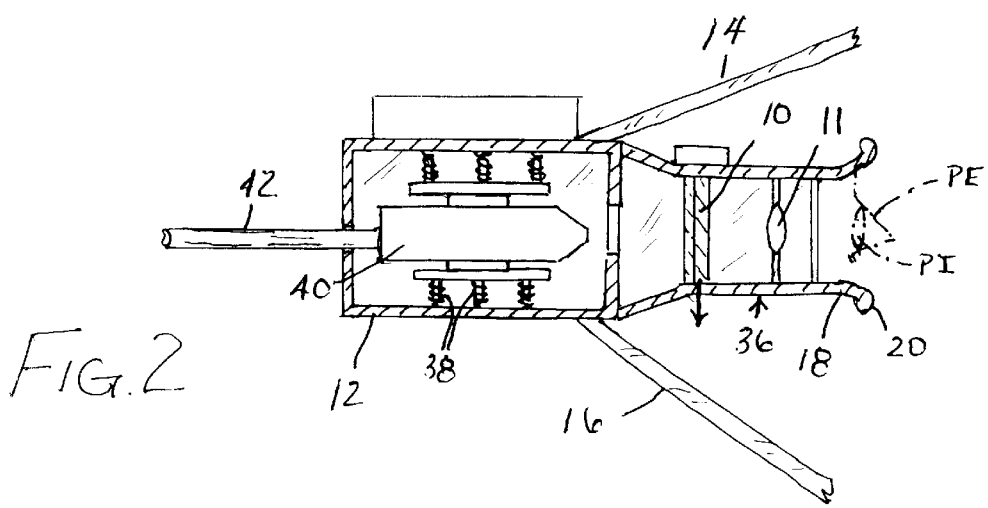
FIG. 2 is a schematic cross-sectional view of selected components of the apparatus of FIG. 1.
Figure 3:
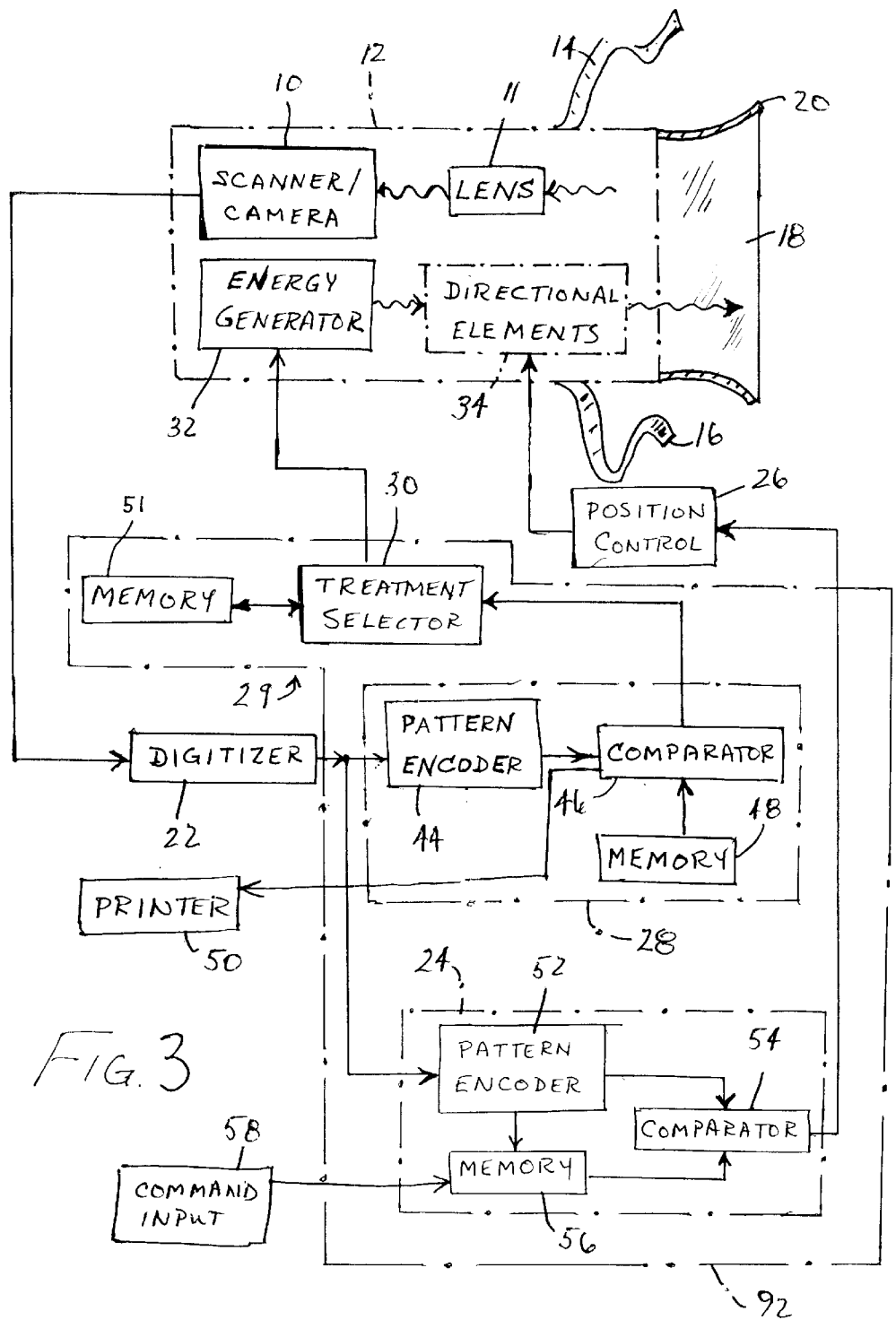
FIG. 3 is a block diagram similar to FIG. 1, showing further details of a diagnostic-and therapeutic apparatus in accordance with the present invention.

Elements of the apparatus of FIG. 1 which are shown in FIG. 2 or 3 are designated by the same reference numerals. As illustrated in FIG. 2, skirt 18 is provided at the free end of a tubular eyepiece part 36 attached to housing 12. Directional components 34 include a plurality of electromagnetic actuator coils 38 for controllably pivoting an energy emitter 40. Emitter 40 may be a source of laser energy, in which case emitter 40 is energized via a power cable 42 and constitutes energy generator 32 (FIG. 1). Alternatively, emitter 40 may be an output for laser energy transmitted via a fiber optic cable (42) from energy generator 32 (FIG. 1), which is located outside of housing 12.

As illustrated more specifically in FIG. 3, diagnostic component 28 may comprise a pattern encoder 44 which analyzes raw digitized data from video camera 10 and digitizer 22 to determine the shapes, locations and color characteristics of patterns in the patient's iris. The analyzed and encoded pattern data is fed to a comparator 46 which compares the incoming pattern data with previously generated pattern data stored in a memory 48. Upon determining a closest match between the incoming pattern data for the individual patient and the stored pattern data, comparator 46 transmits, to treatment selector 30, a signal encoding a diagnostic evaluation of the pattern data. The diagnostic evaluation may be output via a printer 50 connected to comparator 46.

Treatment selector 30 may access a dedicated memory 51 for determining, in response to the diagnostic information from comparator 46, an iris zone ZN (FIG. 1) and a schedule of treatment with energy from generator 32. More specifically, the treatment schedule may include amounts and durations of energy pulses.

As further illustrated in FIG. 3, position tracking component 24 may comprise a pattern encoder 52 which analyzes raw digitized data from video camera 10 and digitizer 22 to determine the shapes, locations and color characteristics of features of the patient's eye. The features monitored by encoder 52 may be different than the patterns detected by encoder 44. For example, encoder 52 may be adapted to track the overall shape of the iris, as well as a limited number of key features thereof. The analyzed and encoded pattern data from encoder 52 is fed to a comparator 54 which compares the incoming pattern data with previously generated pattern data stored in a memory 56. Pattern encoder 52 is directly connected to memory 56 for feeding thereto a reference pattern for the particular patient. For example, the patient may be instructed to stare in a preselected direction. A command from an external input 58 induces storage of the incoming pattern in memory 56 for comparison with subsequently arriving pattern data to determine the instantaneous position or orientation of the patient's eye PE (FIG. 1).

Figure 4:
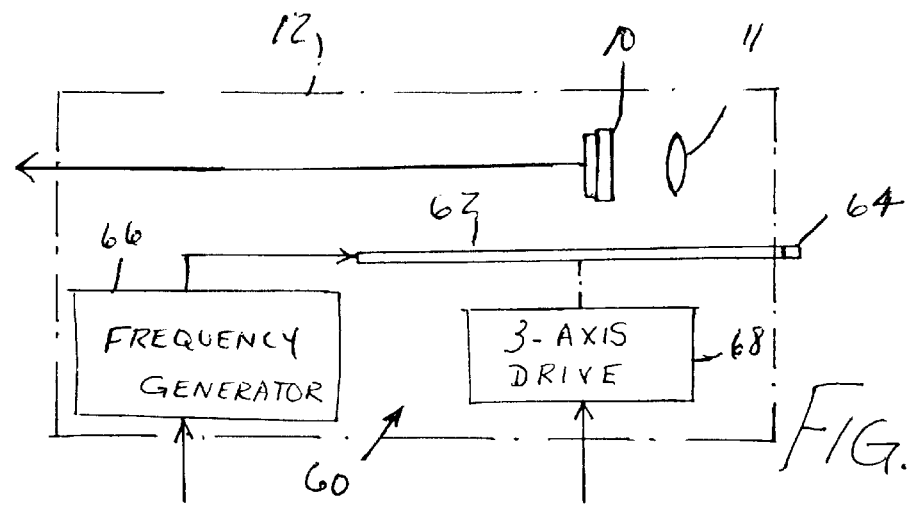
FIG. 4 is a diagram of some particular elements for implementing the apparatus of FIGS. 1 and 3.
Figure 5:
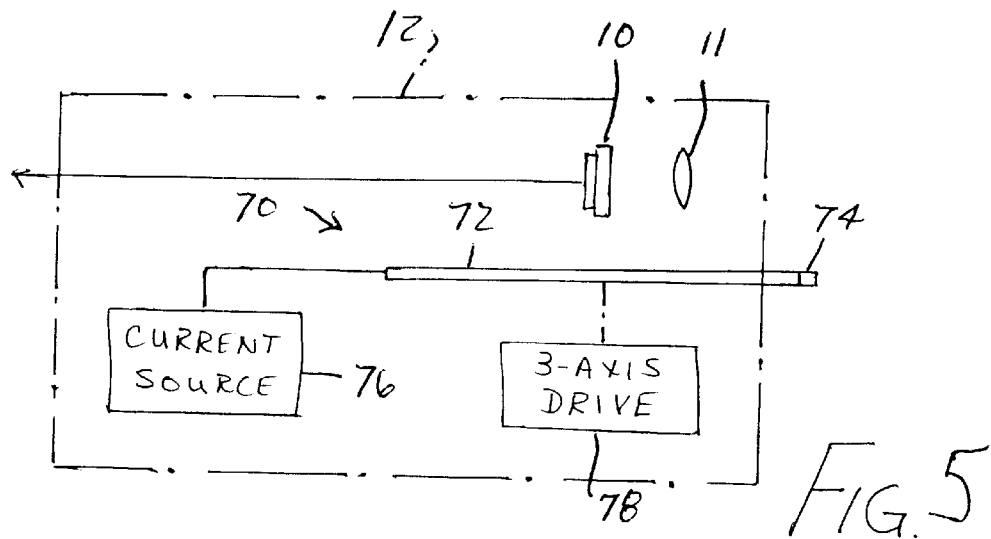
FIG. 5 is a diagram of an alternative embodiment for implementing the apparatus of FIGS. 1 and 3.
Figure 6:
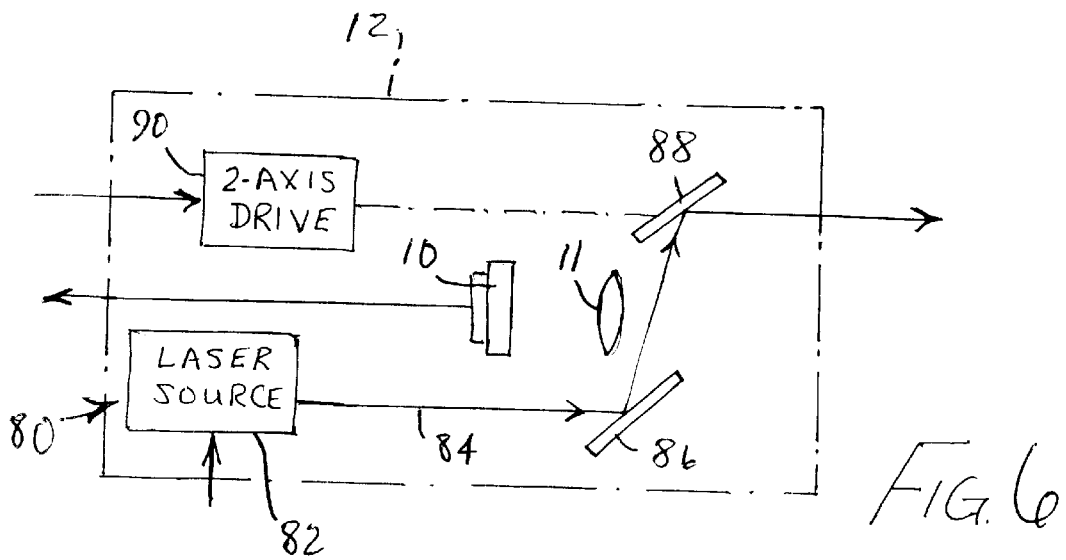
FIG. 6 is a diagram of another alternative embodiment for implementing the apparatus of FIGS. 1 and 3.

Elements of the apparatus of FIGS. 1 and 3 which are shown in FIG. 4–6 are designated by the same reference numerals. As illustrated in FIG. 4, an iris treatment apparatus may comprise an energy applicator 60 including a rod 62 provided at an end with a piezoelectric crystal 64. Crystal 64 produces a pressure wave in response to an acoustic-frequency electrical signal from a signal generator 66. Rod 62 is positioned proximately to a patient's iris by a 3-axis drive 68 which may be magnetic (solenoids), electromagnetic (motors), pneumatic, or hydraulic.

As depicted in FIG. 5, another iris treatment apparatus may comprise an energy applicator 70 including a rod 72 provided at an end with a heating element 74. Heating element 74 produces heat energy in response to a voltage from a current source 76. Rod 72 is positioned proximately to a patient's iris by a magnetic, electromagnetic, pneumatic, or hydraulic 3-axis drive 78.

As shown in FIG. 6, a laser treatment apparatus comprises an energy applicator 80 including a laser source 82 emitting a laser beam 84 which is directed via mirrors 86 and 88 towards a selected target zone ZN (FIG. 1) of a patient's iris. At least one mirror 88 is pivoted by a drive 90 to properly aim the collimated electromagnetic wave energy from source 82.

It is possible, of course, to include all of the energy applicators 60, 70, and 80 (FIGS. 4, 5, and 6) in the same iridological treatment device. It is even possible to treat different zones of the iris simultaneously with different treatment modalities, i.e., heat, pressure waves, and light energy. Another possible modality is magnetic: an electromagnet at the distal end of a movable rod produces a magnetic field with a controllable flux.

Figure 7:
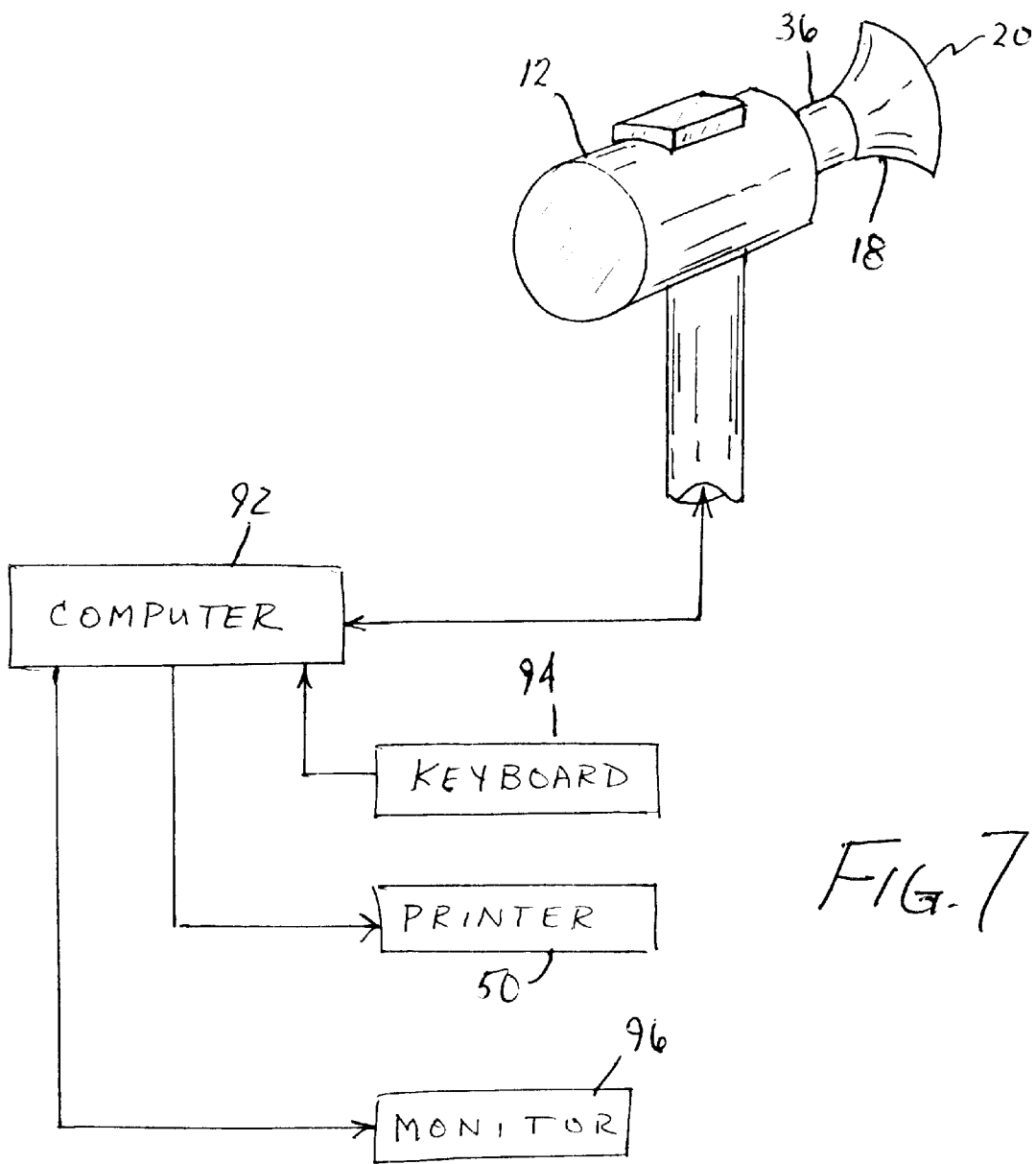
FIG. 7 is partially a schematic perspective view and partially a block diagram of a diagnostic and therapeutic apparatus in accordance with the present invention.

FIG. 7 depicts a further iris treatment apparatus wherein the automatic diagnostic and treatment selection functions of diagnostic component 28 and treatment selector 30 and the locating function of position tracking unit 24 are performed by a specially programmed digital computer 92. Computer 92 can thus be viewed as encompassing diagnostic component 28 treatment selector 30, and position tracking unit 24, as illustrated in FIG. 3. The command input 58 of FIG. 3 may take the form of a keyboard 94, while a monitor 96 is connected to computer 92 for providing a video picture of the patient's iris PI (FIG. 1) with highlighted or otherwise identified features of interest.

It is possible for a therapist to use monitor 96 and keyboard 94, as well as other input command devices such as a mouse (not shown), to select a zone ZN of the patient's iris PI for treatment and to instruct computer 92 as to a preferred treatment schedule. More particularly, the therapist may select the kind of energy (acoustic, heat, light), the intensity and the duration, as well as frequency (in the case of waveform energy) and periodicity of repetitive energy application.

In treating a patient via the patient's iris, a zone ZN of the patient's iris PI is first selected, either manually via keyboard 94 or other input peripheral or automatically by computer 92 or treatment selector 30. The patient's eye is monitored via position tracking unit 24 to determine an instantaneous or real-time position of the selected zone ZN. In accordance with the position of the zone determined by position tracking unit 24, position control unit 26 induces directional or guide elements 34 to direct, towards the selected target zone ZN, energy of a magnitude and duration determined by treatment selector 30.

Iris zone ZN may be selected in part by operating video camera 10 to automatically scan the patient's iris PI and generate a video signal encoding patterns in the iris. Comparator 46 of diagnostic component 28 automatically compares pattern data in the video signal with prestored pattern data in memory 48 to derive diagnostic information pertaining to the individual patient. Different kinds of possible diagnoses can be appreciated by a review of the booklet "Iridology Simplified," by Bernard Jensen (1980), published by Iridologists International of 24360 Old Wagon Road, Escondido, Calif. 92027.

The target zone ZN of the patient's iris PI may be selected automatically by treatment selector 30 in response to the diagnostic information from diagnostic component 28. As discussed hereinabove with reference to FIG. 7, the diagnosis and treatment selection may be made by computer 92 which is programmed with statistical data correlating iris patterns of hue and light or darkness levels with physiological states of different organs and with possible treatments to counteract undersirable conditions.

It is possible for treatment selector 30 to automatically select characteristics of the energy applied, including intensity and duration of application, to treat a patient. Where the energy is waveform energy such as light or, more generally, electromagnetic energy, or acoustic energy, characteristics such as frequency, intensity and wavelength, as well as possibly polarization, may be varied according to the diagnostic information.

Although the invention has been described in terms of particular embodiments and applications, one of ordinary skill in the art, in light of this teaching, can generate additional embodiments and modifications without departing from the spirit of or exceeding the scope of the claimed invention. For example, a supplemental or alternative treatment modality may be chemical: a preselected chemical composition may be ejected from a controllably positionable dispenser nozzle to a predetermined region of the iris for treating a patient. If the chemical composition is in an aqueous solution, the temperature of that solution may be controlled for purposes of simultaneously effectuating an iridological heat treatment. Of course, a heat treatment may be implemented separately, with a simple aqueous solution or a gas dispensed from a nozzle and the temperature of the liquid or gas may be varied above or below body temperature to treat the patient.

Monitoring the position of the patient's eyeball for purposes of tracking the location of one or more selected iris zones may be accomplished by techniques other than the video pattern recognition procedure detailed hereinabove. For example, the contour of the eyeball may be scanned from a plurality of locations, the different contours being analyzed to determine the orientation of the eyeball.

It is to be noted that eye position tracking and iris pattern examination may be implemented via wavelength ranges extending beyond the optical, for example, into the infrared regions of the spectrum.

Accordingly, it is to be understood that the drawings and descriptions herein are offered by way of example to facilitate comprehension of the invention and should not be construed to limit the scope thereof.

What is claimed is:

1. A method for diagnosing a patient, comprising:

automatically scanning a patient's iris to generate an electrical signal encoding patterns in the iris; and automatically comparing pattern data in said signal with previously stored pattern data to derive diagnostic information pertaining to the patient.

2. The method defined in claim 1 wherein the scanning of the patient's iris includes attaching a scanner apparatus to the patient's head and operating the scanner apparatus to generate said signal.

3. The method defined in claim 1 wherein said signal is a video signal and the automatic scanning of the patient's iris includes aiming a video camera at the iris and operating the video camera to generate said signal.

4. The method defined in claim 1 wherein said stored pattern data is stored in a memory of a computer, further comprising digitizing said signal and transmitting the digitized signal to said computer, the comparing of the pattern data in said signal with previously stored pattern data including the step of operating the computer.

5. The method defined in claim 1, further comprising printing out the derived diagnostic information on a sheet.

* * * * *